United States Patent [19]

Vartan

[11] Patent Number: 5,114,929
[45] Date of Patent: May 19, 1992

[54] PHARMACEUTICAL FORMULATION

[75] Inventor: Robert R. Vartan, Bristol, Tenn.

[73] Assignee: Beecham Group p.l.c., England

[21] Appl. No.: 484,662

[22] Filed: Mar. 1, 1990

Related U.S. Application Data

[63] Continuation-in-part of Ser. No. 326,619, Mar. 21, 1989, abandoned.

[51] Int. Cl.⁵ .................. A01N 43/04; A61K 31/43; A61K 31/545
[52] U.S. Cl. ...................... 514/29; 514/192; 514/196; 514/198; 514/199; 514/200; 514/210; 514/937; 514/938
[58] Field of Search .............. 514/29, 192, 196, 198, 514/199, 200, 210, 937, 938; 424/45

[56] References Cited

U.S. PATENT DOCUMENTS

| 3,097,135 | 7/1963 | Lynch | 514/29 |
| 4,079,128 | 3/1978 | Lin et al. | 424/181 |
| 4,672,056 | 6/1987 | Fernandes et al. | 514/29 |
| 4,725,595 | 2/1988 | Schriewer et al. | 514/211 |
| 4,734,407 | 3/1988 | Schmidt et al. | 514/196 |

FOREIGN PATENT DOCUMENTS 013147 1/1985 European Pat. Off. .
2250680 5/1973 Fed. Rep. of Germany .

Primary Examiner—Nathan M. Nutter
Attorney, Agent, or Firm—Rosenman & Colin

[57] ABSTRACT

An unpressurized container containing a palatable pharmaceutical formulation comprising a homogeneous, non-aqueous suspension of an orally active medicament, an edible oily vehicle, an edible emulsifier and a finely particulate sugar having no oily after taste.

25 Claims, No Drawings

PHARMACEUTICAL FORMULATION

This is a continuation-in-part of U.S. application Ser. No. 326,619, filed Mar. 21, 1989, now abandoned.

The present invention relates to pharmaceutical formulations for oral administration in the treatment of disease conditions.

The most common dosage forms for oral administration of pharmaceutical are tablets and capsules. In recent years however it has become evident that patient compliance with prescribed medication regimens is affected where patients find the taste or size of such dosage forms unacceptable. Alternative forms such as chewable tablets and syrups and suspensions have been developed but these are frequently disliked by patients for grittiness, astringency or unpleasant "mouth feel".

Moreover presently available suspensions generally are packaged as dry powders which require reconstitution with a diluent and must be refrigerated after reconstitution to maintain the potency of the active ingredient over the recommended course of therapy. In such instances if an inaccurate volume of diluent is added to the powder or if the liquid and dry components are not properly mixed, the resultant suspension could provide non-uniform dosing due to "clumping" and/or doses which are either super potent or sub-potent depending upon the amount of diluent added.

U.S. Pat. No. 4,639,367 discloses aerosol-packaged foam whip formulations to provide dosage forms of therapeutic agents which would overcome these disadvantages. These formulations comprise foamable liquid oil, foaming agent and propellant and containing an active therapeutic agent. Such packaging adds significantly to the cost of the medication.

The present invention is based on the discovery that certain non-aqueous suspensions of orally-active medications can be produced which are extremely palatable, have a smooth consistency, are "ready-to-use", i.e., do not require reconstitution, and need not be refrigerated to maintain the potency of the active ingredient. Furthermore, the composition of these suspensions is such that no special production techniques or packaging components are required. Instead standard filling equipment and containers such as plastic or glass bottles may be utilized.

According to the present invention there is provided a pharmaceutical formulation comprising a homogenous, non-aqueous, suspension of an orally active medicament, an edible oily vehicle, an edible emulsifier having a hydrolipophylic balance in the range 2 to 14 and a finely particulate sugar.

In accordance with a further aspect of the invention there is provided an unpressurised container containing a homogenous, non-aqueous, suspension of an orally active medicament, an edible oily vehicle, an edible emulsifier having a hydrolipophylic balance in the range 2 to 14 and a finely particulate sugar said suspension being free of propellant and/or foaming agent.

Pharmaceutical formulations of the present invention may include any orally active medicaments. Particularly preferred formulations incorporate orally active antibiotics, in particular β-lactam and macrolide antibiotics such as penicillins, cephalosporins and erythromycins. Typical β-lactams include amoxycillin trihydrate, sodium amoxycillin amoxycillin anhydrous, ampicillin trihydrate, ampicillin anhydrous, penicillin V, (e.g. PEN V ), esters of ampicillin such as pivampicillin, talampacillin and bacampicillin, other semi-synthetic penicillins such as cloxacillin, dicloxacillin, flucloxacillin, carfecillin, methicillin, nafcillin, azlocillin, mezlocillin, and piperacillin. Suitable cephalosporins may include cephradine and cephalexin. Formulations containing β-lactam antibiotics may optionally incorporate β-lactamase inhibitors such as clavulanic acid. Further suitable antibiotics for incorporation into formulations of the invention may include macrolides such as erythromycin and quinolones. A preferred antibiotic is crystalline sodium amoxycillin as disclosed in European Pat. No. 131147.

Other medicaments which may be incorporated include vitamins, mineral supplements, antihistamines, antitussives, decongestants, local anaesthetics, and antacids. However the invention is of its primary importance when used in the formulation of active ingredients which are poorly stable when prepared as aqueous suspensions.

In the compositions of the present invention the active ingredients (taken as free acid where appropriate) will normally represent 0.1 to 40% w/w, more suitably 1 to 20%, typically 2 to 10%, of the total.

The oily vehicle is suitably an edible vegetable oil such as linseed oil, soybean oil, partially hydrogenated soybean oil, corn oil, sunflower oil; peanut oil, or more preferably fractionated coconut oil. A suitable source of fractionated coconut oil is "Myglyol 812", a triglyceride of fractionated coconut oil of fatty acids $C_8$-$C_{10}$, available from Dynamit-Nobel UK, Slough, Bucks, England. Typically the oily vehicle will constitute from 40 to 85% of the formulation.

The desirable palatability property of formulations of the present invention are provided by the use of an emulsifier having a hydrolipophylic balance (HLB) in the range 2 to 14, more suitable 3 to 10 preferably about 4. Typically, the emulsifier comprises from 0.5 to 7.5% of the total of the formulation, and the consistency of the product may be influenced by the quantity included within this range. Proprietary emulsifiers such as Tweens and Lecithins may be used. However the emulsifier has preferred taste properties when it comprises a high percentage of distilled monoglycerides, preferably greater than 70% monoglyceride and most suitably greater than 90% monoglyceride. A preferred emulsifier for use in the formulation of the invention is Myverol 18-04, which contains a minimum of 90% monoglyceride and has an HLB of about 4. Myverol 18-04 is a product of Eastman. When the formulation includes around 0.5% to 2% Myverol 18-04 the consistency is similar to that of a milk shake. When levels of 5-7.5% are present the consistency approaches that of peanut butter.

The finely particulate sugar used in formulations of the present invention is preferably confectioner's sugar having a particle size of less than 100 micron., most suitably confectioners sugar NF 12X. Other suitable sugars include alcohol sugars such as mannitol, sorbitol or co-crystallised sorbitol-mannitol. Typically the finely particulate sugar comprises 10–40% of the total of the formulation.

Formulations of the invention may also include an effective amount of suitable flavorings and/or sweetening agents such as aspartame, sodium cyclamate, calcium cyclamate or sodium saccharin. Typically an effective amount comprises 0.05 to 1% of the formulation. Where desirable, desiccants and thickening agents may be added such as silicon dioxide (for example Syloid 63)

or colloidal silicon dioxide (for example Cab-O-Sil PTG) typically in amounts of from 0.5 to 5%. It may also be desirable to add suitable preservatives to the formulations. Preferably the preservative is added at a level of from 0.01 to 0.5&. Preferred preservatives for use in formulations of the present invention include methyl paraben, butylparaben, propylparaben, benzoic acid and sorbic acid.

Where the active ingredient is in hydrated form, e.g. amoxycillin trihydrate, it may be desirable to incorporate a dessicant such as molecular sieve in the composition to improve the long term stability.

A preferred $\beta$-lactamase inhibitor for use in compositions of the present invention which contain $\beta$-lactam antibiotics is clavulanic acid, normally used as potassium clavulanate. The alternative suitable $\beta$-lactamase inhibitor may comprise a $\beta$-lactamase inhibiting penem compound such as $(5R)(Z)$-6-(1-methyl-1,2,3-triazol-4-yl-methylene)-penem-3-carboxylic acid and its salts as disclosed in EP-154 132. When potassium clavulanate is present in compositions of the present invention it is essential that a suitable desiccant material is also present.

Also included within the scope of the present invention is a process for the preparation of a pharmaceutical formulation comprising heating together an edible oily vehicle, an edible emulsifier having a hydrolipophylic balance in the range 2 to 14 and a finely particulate sugar, cooling, and adding an orally active medicament and thereafter homogenising the mixture.

Thus in a suitable process for the manufacture of the formulations of the invention the edible oily vehicle, the emulsifier and the sugar are heated together to a temperature of 60 to 70° C., preferably about 65° C. The mixture is then cooled with agitation to a temperature of 27 to 45° C., preferably 28 to 35° C., and the medicament together with any flavoring, preservative and desiccant, is added. The mixture is then homogenised until the product has a smooth consistency. This process produces any extremely palatable product resembling a milk shake and with no taste of oils detectable.

The homogenous suspension is then administered from a bottle into a spoon. A typical formulation will contain from 100 mg to 1 g of medicament per teaspoon, most suitably 200 to 500 mg per teaspoon, preferably 250 mg. The weight in a single teaspoon will preferably be such that the single dose contains sufficient medicament for effective treatment of the disease. The single dose will be repeated according to the usual dosage regime for the medicament.

Some examples will now be described.

EXAMPLE 1

The following composition was prepared:

| Miglyol 812 | 370.625 |
| Amoxycillin Trihydrate 87% (pfa) | 24.0 g |
| Myverol 18-04 | 5.0 g |
| Confectioner Sugar NF 12X | 100.0 g |
| Vanilla Flavor | 0.375 g |

The Miglycol 812, Myverol 18-04 and confectioner's sugar were heated together to 65° C. The mixture was then cooled to 40°–42° C. with agitation and the amoxycillin trihydrate and flavouring added and the mixture homogenised until smooth.

Each 3 g of the formulation (½ teaspoon) contained 125 mg of amoxycillin or 250 mg per teaspoon.

The product was found to have a smooth palatable consistency with no taste of oils.

EXAMPLE 2

The following compositions have been prepared

|  | 250 mg/5 ml | 125 mg/5 ml |
|---|---|---|
| Miglyol 812 | 1706.85 g | 1778.10 g |
| MethylParaben NF | 2.50 g | 2.50 g |
| PropylParaben NF | 1.00 g | 1.0 g |
| Colloidal Silicon Dioxide | 25.00 g | 20.0 g |
| Mannitol Powder | 625.00 g | 625.00 g |
| Aspartame | 2.5 g | 2.50 g |
| Sodium Amoxycillin Crystal 91.6% | 129.40 g | 64.40 g |
| Vanilla Cream Flavor | 1.5 mL | 1.5 mL |
| Bubblegum Flavor | 6.26 mL | — |
| Strawberry Flavor | — | 5.0 mL |
| Total | 2,500.0 g | 2,500.0 g |

The density at 22.5° C. of the 250 mg/5 ml composition was 1.073 g/mL and of the 125 mg/5 ml composition was 1.058 g/mL.

Stability tests have been carried out at 20°, 30° and 37° C. No indication of instability has been given after 8 weeks in the case of these compositions. Accelerated stability tests at 50° C. have shown no instability at less than 6 weeks.

EXAMPLE 3

The following composition has been prepared

|  | 250 mg/5 ml |
|---|---|
| Miglyol 812 | 344.15 g |
| MethylParaben NF | 0.5 g |
| PropylParaben NF | 0.2 g |
| Tween 80 | 1.25 g |
| Colloidal Silicon Dioxide | 1.0 g |
| Mannitol Powder | 125.0 g |
| Aspartame | 0.5 g |
| Amoxycillin Trihydrate 87% | 27.4 g |

The specific gravity at 22.5° C. was 1.065 g/ml

This example has similar smooth consistency and stability to that of Example 1.

I claim:

1. An unpressurized container containing a palatable pharmaceutical formulation comprising a homogenous, non-aqueous suspension of an orally active medicament, an edible oily vehicle, an edible emulsifier having a hydrolipophylic balance in the range 2 to 14 and a finely particulate sugar, said suspension being free of propellant and foaming agent and having no oily aftertaste.

2. A container according to claim 1 wherein the orally active medicament is an antibiotic.

3. A container according to claim 1 wherein the orally active medicament is a penicillin, cephalosporin or erythromycin.

4. A container according to claim 1 wherein the edible oily vehicle is a vegetable oil selected from the group comprising linseed oil, soybean oil, partially hydrogenated soybean oil, corn oil, sunflower oil, peanut oil or fractionated coconut oil.

5. A container according to claim 4 wherein the edible oily vehicle is a triglyceride of fractionated coconut oil of fatty acids $C_8$–$C_{10}$.

6. A container according to claim 1 wherein the edible emulsifier contains greater than 70% distilled monoglyceride.

7. A container according to claim 6, wherein the edible emulsifier is Myverol 18-04.

8. An unpressurized container containing a palatable pharmaceutical formulation comprising a homogenous, non-aqueous suspension of 0.1 to 40% by weight of the total product of an orally active medicament, 0.5 to 7.5% by weight of an edible emulsifier having a hydrolipophilic balance in the range 2 to 14, 10 to 40% by weight of finely particulate sugar, optionally up to 1% of suitable flavoring and/or sweetening agents, up to 5% of desiccants and/or thickening agents and up to 0.5% of a preservative, the balance consisting of an edible oily vehicle being free of propellant and foaming agent and having no oily aftertaste.

9. An unpressurized container containing a palatable pharmaceutical formulation consisting essentially of a homogenous, non-aqueous suspension of 40 to 85% Miglyol 812, 0.5 to 7.5% Myverol 18-04, 10 to 40% confectioner sugar NF12X, up to 0.5% flavoring, up to 0.5% preservative and 1 to 20% of an orally active $\beta$-lactam antibiotic and free of propellant and foaming agent and having no oily aftertaste.

10. A container according to claim 9 wherein the $\beta$-lactam antibiotic is crystalline sodium amoxycillin.

11. A palatable pharmaceutical formulation comprising a homogenous, non-aqueous suspension of an orally active medicament, an edible oily vehicle, an edible emulsifier having a hydrolipophilic balance in the range 2 to 14 and a finely particulate sugar and free of propellant and foaming agent and having no oily aftertaste.

12. A pharmaceutical formulation according to claim 11 wherein the orally active medicament is an antibiotic.

13. A pharmaceutical formulation according to claim 11 wherein the orally active medicament is a penicillin, cephalosporin or erythromycin.

14. A pharmaceutical formulation according to claim 11 wherein the edible oily vehicle is a vegetable oil selected from the group comprising linseed oil, soybean oil, partially hydrogenated soybean oil, corn oil, sunflower oil, peanut oil or fractionated coconut oil.

15. A pharmaceutical formulation according to claim 14 wherein the edible oily vehicle is a triglyceride of fractionated coconut oil of fatty acids $C_8$-$C_{10}$.

16. A pharmaceutical formulation according to claim 11 wherein the edible emulsifier contains greater than 70% distilled monoglyceride.

17. A pharmaceutical formulation according to claim 16, wherein the edible emulsifier is Myverol 18-04.

18. A palatable pharmaceutical formulation comprising a homogenous, non-aqueous suspension of 0.1 to 40% by weight of the total product of an orally active medicament, 0.5 to 7.5% by weight of an edible emulsifier having a hydrolipophilic balance in the range 2 to 14, 10 to 40% by weight of finely particulate sugar, optionally up to 1% of suitable flavoring and/or sweetening agents, up to 5% of desiccants and/or thickening agents and up to 0.5% of a preservative, the balance consisting of an edible oily vehicle being free of propellant and foaming agent and having no oily aftertaste.

19. A palatable pharmaceutical formulation consisting essentially of a homogenous, non-aqueous suspension of 40 to 85% Miglyol 812, 0.5 to 7.5% Myverol 18-04, 10 to 40% confectioner sugar NF12X, up to 0.5% flavoring, up to 0.5% preservative and 1 to 20% of an orally active $\beta$-lactam antibiotic and free of propellant and foaming agent and having no oily aftertaste.

20. A pharmaceutical formulation according to claim 19 wherein the $\beta$-lactam antibiotic is crystalline sodium amoxycillin.

21. The container according to claim 1 wherein said formulation has the consistency resembling a milk shake.

22. The container according to claim 8 wherein said formulation has a consistency resembling a milk shake.

23. The container according to claim 9 wherein said formulation has a consistency resembling a milk shake.

24. The formulation according to claim 11 having a consistency resembling a milk shake.

25. The formulation according to claim 18 having a consistency resembling a milk shake.

* * * * *